United States Patent [19]

Mazzara

[11] Patent Number: 5,222,943
[45] Date of Patent: Jun. 29, 1993

[54] SELFLOCKING SYRINGE
[75] Inventor: Isidoro Mazzara, Campofranco, Italy
[73] Assignee: Profarm S.p.A., Caltanisetta, Italy
[21] Appl. No.: 852,286
[22] Filed: Mar. 16, 1992
[51] Int. Cl.$^5$ .............................................. A61M 5/00
[52] U.S. Cl. ...................................... 604/110; 604/195
[58] Field of Search ................ 604/110, 187, 195, 198

[56]  References Cited
U.S. PATENT DOCUMENTS

| | | |
|---|---|---|
| 4,874,382 | 10/1989 | Lindemann et al. ............. 604/198 X |
| 4,955,870 | 9/1990 | Ridderheim et al. ................ 604/195 |
| 5,084,029 | 1/1992 | Tagliaferri et al. ................. 604/195 |

Primary Examiner—John D. Yasko
Attorney, Agent, or Firm—McGlew & Tuttle

[57]  ABSTRACT

The invention regards a selflocking syringe. The syringe rod (13) is equipped with an extractor (15) which, when the syringe plunger (12) is pushed to the end of the stroke, hooks (15b) the needle (11) and withdraws it by means of a preloaded spring (16) to the inside of the rod (13), into a protected and inaccessible position, thus making the syringe unserviceable already after its first use.

3 Claims, 2 Drawing Sheets

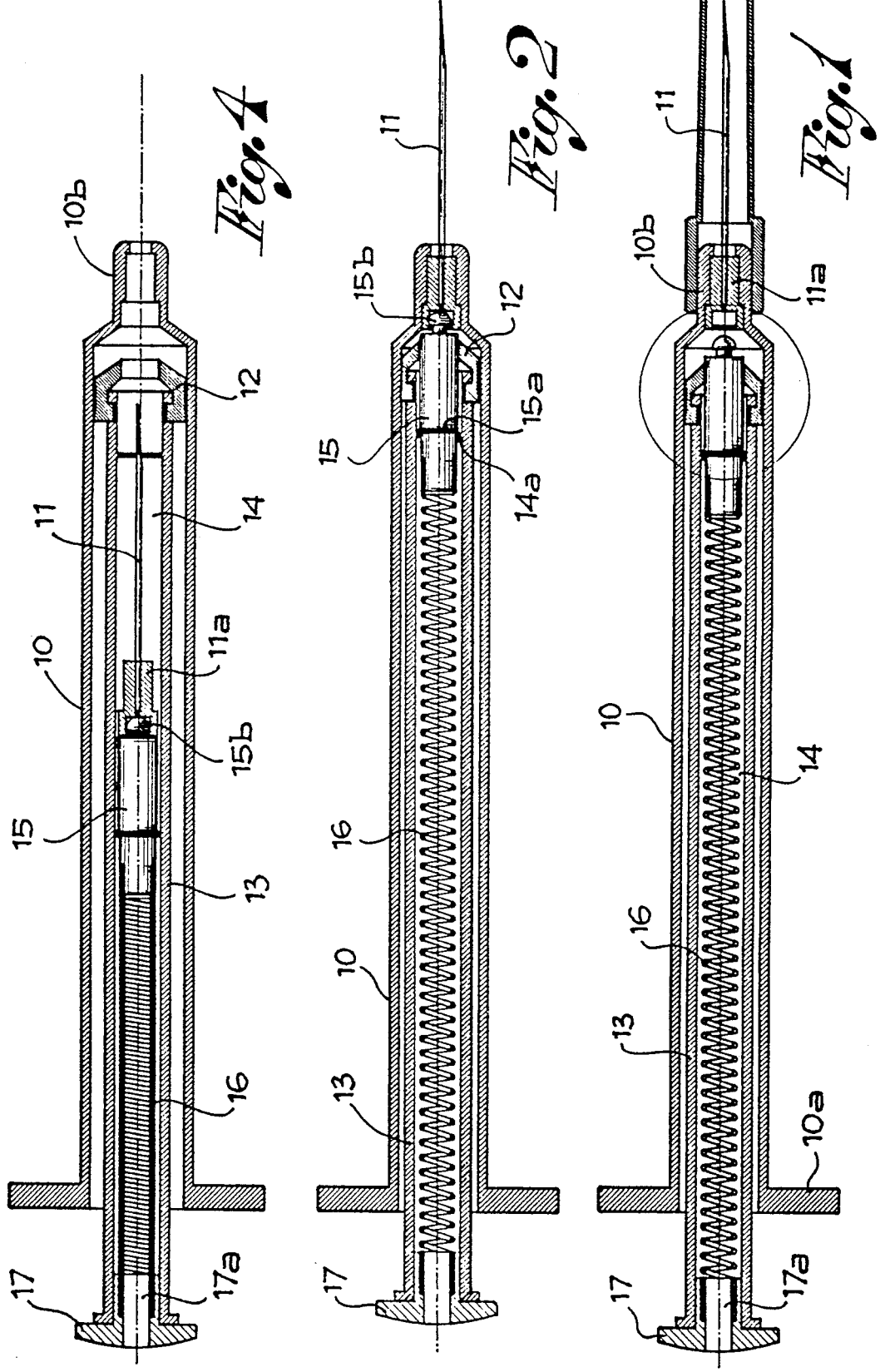

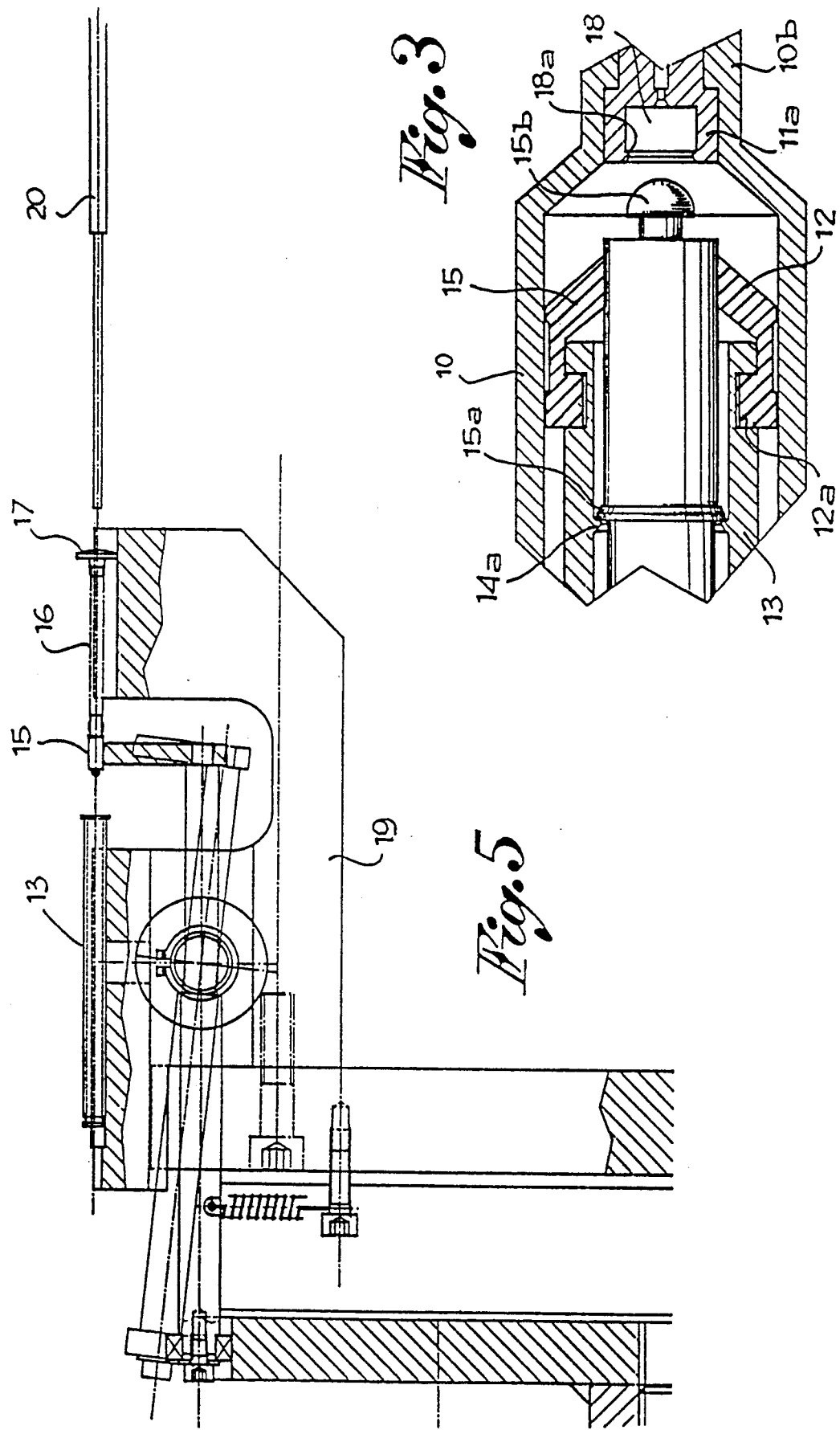

SELFLOCKING SYRINGE

FIELD OF THE INVENTION

The present invention regards selflocking syringes, with particular reference to a syringe with a needle which disappears thus becoming inaccessible after the use of the syringe.

BACKGROUND OF THE INVENTION

The dangers originating from the reutilization of already used syringes and the problems caused by the abandonment in public places of used syringes complete with needle are well-known, especially the damages which any prick of these syringes may cause to anybody who picks up and inadvertently handles abandoned syringes.

SUMMARY AND OBJECTS OF THE INVENTION

One of the tasks of the present invention is to eliminate the mentioned dangers and to solve efficaciously the problems caused by syringes, from the one hand by making substantially unserviceable the syringe after its first use and, from the other hand, by getting the syringe needle such that it has disappeared thus preventing it from remaining exposed, which represents a potential danger when abandoning the syringe.

Another task of the invention is to supply a syringe incorporating some means which, without affecting the normal use of the syringe, are able to withdraw the needle into the plunger automatically so as to make it inaccessible from outside, already after the first use of the syringe. This way, the syringe becomes unserviceable and its needle, being completely hidden, cannot cause any damages.

The proposed syringe essentially consists of a cylinder ending by a nose to which a needle is applied and of a plunger sliding in the cylinder and equipped with an operation rod. In compliance with the invention, in this syringe:

the needle is applied to the cylinder nose by means of a needle-holder introduced and extractable from the inside of the cylinder;

the rod and the plunger have got an axial through hole in which a sliding extractor and a recovery spring are arranged; the spring is connected to this extractor and to a plug applied on the free end, that is the outer end, of the rod;

the extractor can be displaced from an advanced position, towards the plunger, to a back position; it shows a head protruding axially from the plunger and is conceived to hook the needle-holder when the plunger is pushed deeply into the cylinder;

in the advanced position, the extractor is integral with the rod and keeps the spring under tension through some hooking means which can be disengaged, at least partially, when the plunger is pushed deeply and the extractor head has hooked the needle-holder;

after the disengagement of these hooking means, the extractor shifts to the back position by means of the spring in order to withdraw the needle-holder and the needle into the inner part of the rod.

Advantageously, the forging ends of the recovery spring are let, that is constrained, into the material composing the extractor and the end plug applied on the rod.

Anyhow, further details about the invention will be more evident in the description given below which refers to the enclosed drawing showing an indicative and non-limiting example of practical realization of the selflocking syringe.

BRIEF DESCRIPTION OF THE DRAWINGS

In this drawing:

FIG. 1 shows, in longitudinal section, the syringe before use and with the needle protected by means of a cap;

FIG. 2 shows, in longitudinal section, the syringe in the use conditions;

FIG. 3 shows a magnified detail of a part of the syringe marked with a circle in the picture 1;

FIG. 4 shows, in longitudinal section, the syringe after use, that is with withdrawn needle;

FIG. 5 shows an example of the equipment used to make ready the plunger with extractor rod and recovery spring.

DETAILED DESCRIPTION OF THE PREFERRED EMBODIMENTS

The syringe at issue essentially consists of a hollow cylinder 10, a needle 11 and a plunger 12 with a respective operation rod 13.

The cylinder 10 shows at the back a seizing flange 10a and ends on the front side by a nose 10b to which the needle 11 is applied. This needle is applied to a needle-holder 11a which is introduced like a plug into a seat defined by the nose 10b from the inside of the cylinder 10 and which is extractable, as stated below, towards the inside of the cylinder. The plunger 12 slides with tightness into the cylinder 10 and is steadily constrained, in 12a, to the rod 13 which extends and protrudes towards the rear side of the cylinder, beyond the seizing flange 10a.

The rod 13 and the plunger 12 are provided with an axial through hole 14 in which an extracting element 15 and a recovery spring 16 are assembled. The extractor 15 can slide in this through hole 14 and shift from an advanced position, at the same level as the plunger 12, to a back position, far from the plunger. The opposite ends of the recovery spring 16 are respectively fastened to the extractor 15 and to a plug 17 applied on the free, that is rear, end of the rod 13. Advantageously, the forging ends of the recovery spring 16 are let, and so fastened, into the material composing the extractor 15 and the end plug 17. Therefore, the three component parts 15, 16, 17 remain permanently connected and can be handled and assembled jointly and easily.

In its advanced position, the extractor 15 is integral with the rod 13 and keeps the spring 16 loaded since the latter is stretched, having its opposite end fastened and clamped with the plug 17, as it is possible to infer from FIGS. 1 and 2 of the drawing.

For its stop in the advanced position, the extractor 15 is provided with a peripheral step 15a —FIG. 3—which engages itself in the shoulder collar 14a obtained in the hole 14 of the rod 13 thus normally preventing the extractor 15 from shifting backwards. Furthermore, this extractor is equipped with a hooking head 15b, for example in the shape of a mushroom, turned towards the needle-holder 11a and protruding from the piston 12 when the extractor is in the advanced position. The hooking head 15b of the extractor 15 must get constrained with the needle-holder 11a when the plunger is pushed deeply into the cylinder. For this constraint, the needle-holder 11a is provided with a rear notch 18 having at least an inner projection 18a, for example annular, with which the hooking head 15b spring joins together when the plunger reaches the end of the stroke.

In the end, it should be noted that the shoulder collar 14a in the hole 14 of the rod 13 must become deformed, be drawn and destroyed on the step 15a of the extractor 15 when the plunger 12 is pushed deeply into the cylinder and the extractor 15 is hooked to and supported against the needle-holder 11a.

In the syringe described above, the extractor 15, the spring 16 and the plug 17, connected one with the other, are previously assembled into the rod 13 by means of an equipment 19 such as the one represented in the picture 5 so that the extractor 15 is hooked in the advanced position and the spring 16 is loaded, that is under tension. Such an assembly is carried out with the help of a thrust tool 20 which passes through a hole 17a obtained in the plug 17 and which is supported and pushes against the extractor until it gives rise to the hooking of the latter one to the collar 14a and the introduction of the spring and plug into the rod. The hole 17a of the plug 17 can be closed. Subsequently, after applying the plunger 12 to the rod provided with the described equipment, the whole is introduced into the cylinder 10 already equipped with needle 11.

The syringe is now ready for packaging and for a following use as a normal syringe.

However, with this syringe, the needle 11 is withdrawn upon its use to the inside of the rod 13 thus making the syringe unserviceable and the needle inaccessible. As a matter of fact, when the plunger, advancing during the injection, reaches the end of the stroke, the head 15b of the extractor 15 spring hooks the needle-holder and, when pushing on the rod deeply, the collar 14a in the rod 13 on the step 15a of the extractor itself becomes deformed and is drawn. Then, the extractor, no longer constrained to the rod 13, is shifted to the back position by means of the preloaded recovery spring 16 and pulls away the needle hooked through the needle-holder, as shown in FIG. 4 of the drawing.

I claim:

1. A selflocking syringe, comprising:
a hollow syringe cylinder body defining an interior cylindrical plunger cavity and an interior cylindrical nose end; a cylindrical needle holder positioned in said nose end, said needle holder having an interior end defining a step surrounding a needle holder interior cavity and said nose end having an interior step surface preventing said needle holder from moving in an outward direction and allowing said needle holder to be extracted from inside of said plunger cavity; a plunger positioned within said plunger cavity; a rod connected to said plunger, said rod extending into said plunger cavity, each of said rod and said plunger having an axial hole passing therethrough; a sliding extractor positioned within said axial hole of said plunger and within said hole of said rod; a recovery tension spring positioned within said hole of said rod and connected to said sliding extractor; a plug applied to a free end of said rod, said extractor being movably displacable from an advanced position, partially surrounded by said plunger with a portion protruding from said plunger in a needle holder direction, and a retracted position, fully retracted into said rod, positioned away from said needle holder, said extractor having a hooking head protruding from said plunger in said advanced position; hooking means defining connection between said rod and said extractor, maintaining said extractor in said advanced position, said spring being positioned between said plug and said extractor and being maintained under tension in said advanced position, said hooking means including a step formed on a peripheral surface of said extractor, said step interacting with a shoulder collar formed on an interior surface of said rod, said hooking head of said extractor engaging said needle holder interior cavity of said to join said extractor to said needle holder in said advanced position whereby said hooking means disengages said connection of said peripheral step and said shoulder collar allowing said recovery spring to withdraw said needle holder and needle to the inside of said rod, said plug having a hole allowing access to an interior of said rod for passage of a thrust tool for manipulating said extractor and for loading said recovery spring, said recovery spring being fastened into material composing said extractor and being fastened into material composing said end plug to define a three component part set including said retractor, said spring and said end plug which remain permanently connected thereby facilitating handling and assembling.

2. Selflocking syringe in accordance with claim 1 in which the hooking head (15a) engages itself in a notch obtained in the needle-holder and provided with a projection (18a) in which the head spring engages itself.

3. The selflocking syringe, comprising:
a sub assembly including an extractor with a hooking head, a tension spring and a plug, said spring extending into the material forming said extractor and extending into the material forming said plug; a rod with a through hole extending therethrough said rod having a plunger end and an opposite free end; a plunger connected to said rod plunger end, said plunger having a through hole cooperating with the through hole of said rod; a syringe cylindrical body including a first cylindrical portion for housing said plunger and said rod and including a needle cylindrical portion, said needle cylindrical portion defining a needle tip end with an opening, an interior cylindrical portion of reduced diameter and a stepped portion; a needle holder having a first diameter for fitting snugly in said needle tip reduced diameter portion and having a stepped portion for engaging said step portion of said syringe cylindrical housing, said step portion defining an interior engaging portion with a peripheral lip, said needle holder including a through bore supporting a needle; disengagable and engagable hooking means including a step formed on a peripheral portion of said extractor and a shoulder collar formed on an interior surface of said through bore of said rod, said peripheral step of said shoulder collar interacting to define an engaged position wherein said extractor is maintained with a portion surrounded by said plunger and with said hooking head extending out of said plunger in a needle direction and a disengaged position wherein said extractor is free to move relative to said plunger and said rod; a thrust tool passing through said hole of said plug for supporting and pushing against said extractor to effect engagement of said hooking means by interaction of said peripheral step and said shoulder collar for positioning said extractor in said advanced position and loading said spring upon engaging of said plug with said rod free end.

* * * * *